(12) United States Patent
Boast et al.

(10) Patent No.: US 8,695,679 B2
(45) Date of Patent: Apr. 15, 2014

(54) USER ACCESS PORT FOR CONTROLLED ATMOSPHERE APPARATUS

(75) Inventors: David Boast, Shipley (GB); Evan Jonathan Kitsell, Shipley (GB)

(73) Assignee: Don Whitley Scientific Ltd., West Yorkshire (GB)

( * ) Notice: Subject to any disclaimer, the term of this patent is extended or adjusted under 35 U.S.C. 154(b) by 178 days.

(21) Appl. No.: 13/380,447

(22) PCT Filed: Jun. 23, 2010

(86) PCT No.: PCT/GB2010/001242
§ 371 (c)(1),
(2), (4) Date: Dec. 22, 2011

(87) PCT Pub. No.: WO2010/149974
PCT Pub. Date: Dec. 29, 2010

(65) Prior Publication Data
US 2012/0096773 A1    Apr. 26, 2012

(30) Foreign Application Priority Data
Jun. 24, 2009    (GB) .................................. 0910936.4

(51) Int. Cl.
*E06B 3/32* (2006.01)

(52) U.S. Cl.
USPC .............................. 160/90; 435/303.1; 600/22

(58) Field of Classification Search
USPC ................ 160/89, 90; 312/1; 435/303.1, 809, 435/303.2; 600/22
See application file for complete search history.

(56) References Cited

U.S. PATENT DOCUMENTS 2,360,554 A    10/1944  Englert
2,695,605 A *  11/1954  Gibbon ........................... 600/22

(Continued)

FOREIGN PATENT DOCUMENTS

DE    36 17 860    12/1987
EP    0 206 469    12/1986

(Continued)

OTHER PUBLICATIONS

International Search Report for International Application No. PCT/GB2010/001242, mail date Jan. 31, 2011, 3 pages.

(Continued)

*Primary Examiner* — Katherine Mitchell
*Assistant Examiner* — Johnnie A Shablack
(74) *Attorney, Agent, or Firm* — Foley & Lardner LLP (57) ABSTRACT

The invention relates to a user access port for a controlled atmosphere apparatus comprising a porthole extending through a wall; a sealing assembly comprising a first sealing means and a second sealing means for maintaining a sealing barrier across the porthole, whereby the first sealing means comprises a first closure member that is adapted to at least substantially seal the porthole when arranged in a closed position and allow user access to the porthole when arranged in an open position; the second sealing means is mounted so as to extend at least substantially across the porthole and comprises a sealed access member and a second closure member, whereby the sealed access member comprises a user access aperture having a peripheral edge adapted to form a sealing contact with an arm of a user when an operator extends his arm through the user access aperture and whereby the second closure member is adapted to at least substantially seal the user access aperture when arranged in a closed position and at least substantially open the user access aperture when arranged in an open position. The invention further relates to a controlled atmosphere apparatus comprising one or more user access ports, a sealing assembly for a user access port and a method of replacing a sealing means of a user access port.

20 Claims, 9 Drawing Sheets

(56) References Cited

U.S. PATENT DOCUMENTS

| | | | |
|---|---|---|---|
| 2,708,927 | A | 5/1955 | Dixon et al. |
| 2,720,387 | A | 10/1955 | Dorsak |
| 2,803,370 | A | 8/1957 | Lennard |
| 3,117,009 | A | 1/1964 | Boelter |
| 4,669,410 | A | 6/1987 | Howell |
| 4,697,854 | A | 10/1987 | Lunsford |
| 4,936,824 | A * | 6/1990 | Koch et al. ............. 600/22 |
| 5,861,305 | A * | 1/1999 | Silley et al. ............. 435/286.6 |
| 6,293,902 | B1 | 9/2001 | Hundertmark |
| 7,325,890 | B2 * | 2/2008 | Oyama et al. ............ 312/1 |
| 8,186,775 | B2 * | 5/2012 | Sheldon .................... 312/1 |
| 2004/0050117 | A1 | 3/2004 | Geyer et al. |
| 2006/0132376 | A1 | 6/2006 | Coberly |
| 2012/0184028 | A1* | 7/2012 | Swanson et al. .......... 435/303.1 |

FOREIGN PATENT DOCUMENTS

| | | |
|---|---|---|
| EP | 0 411 794 | 2/1991 |
| EP | 1 762 650 | 3/2007 |
| FR | 2590198 | 5/1987 |
| JP | 11-030487 | 2/1999 |
| WO | WO-88/07574 | 10/1988 |
| WO | WO-96/11092 | 4/1996 |

OTHER PUBLICATIONS

Search Report for UK Application No. GB0910936.4, dated Oct. 21, 2009, 4 pages.

International Preliminary Report on Patentability and Written Opinion of the International Searching Authority for PCT/GB2010/001242, issued Jan. 4, 2012, 6 pages.

* cited by examiner

USER ACCESS PORT FOR CONTROLLED ATMOSPHERE APPARATUS

This Application is a U.S. national stage of and claims priority to and the benefit of International Application No. PCT/GB2010/001242, entitled "User Access Port for Controlled Atmosphere Apparatus," filed on Jun. 23, 2010 which claims priority from and the benefit of GB Application No. 0910936.4, filed Jun. 24, 2009, both of which are incorporated herein by reference in their entirety.

A. FIELD OF INVENTION

This invention relates to controlled atmosphere apparatus. More specifically, the invention relates to user access ports for controlled atmosphere apparatus.

B. BACKGROUND TO INVENTION

Controlled atmosphere apparatus or equipment is useful where a prescribed atmosphere must be maintained. Such apparatus is useful in a number of different industries and applications. For example, a controlled atmosphere apparatus having an anaerobic atmosphere may be useful in microbiological laboratories in the process of aiding the identification of certain types of bacteria. A controlled atmosphere apparatus having an atmosphere that resembles the conditions inside the body may be useful in incubating zygotes as part of the In Vitro Fertilisation (IVF) procedure.

A controlled atmosphere apparatus typically comprises at least one chamber with a prescribed atmosphere. The prescribed atmosphere within the chamber is commonly created and maintained by regulating the temperature, humidity and gas concentrations.

It will be appreciated that a controlled atmosphere apparatus must be designed to allow for the manual manipulation of specimens (for example, the loading, unloading and inspection of specimens) without any deleterious effects to the atmosphere within the chamber. Previously, this has been achieved by providing one or more user access ports comprising a long glove or gauntlet sealed to a porthole. The glove is extendable into the chamber from the porthole of the user access port so as to allow an operator to manipulate a specimen within the chamber. Although the glove prevents both the ingress of air into the chamber and outflow of gas from the cabinet, this solution is not ideal because air becomes trapped within the glove as the operator extends his arm and hand into the glove and so his movement is restricted. Also, due to the nature of the glove, the operator's sensitivity of touch is somewhat limited. Moreover, operators complain that their hand becomes clammy when wearing the gloves for a given period of time.

Some of the problems associated with using gloves may be overcome by alternatively providing one or more user access ports with an arm tube comprising an open cuff (bare-hand type tubes). The arm tube is extendable into the chamber from the porthole of the user access port and the open cuff is configured to allow the operator's hand to extend through the arm tube and provide a seal around an operator's arm or wrist such that he can use his bare hand to manipulate a specimen within the chamber. Although the arm tube provides improvements over the gloves, air still becomes trapped within the arm tube as the operator extends his hands and arms through the arm tubes. Hence, an operator's movement is restricted. Critically, there is also a risk that air may ingress into the chamber and gas may leak from the chamber as the operator extends his hand through the open cuff and/or if the seal between the open cuff and the operator's arm or wrist is not maintained.

Accordingly, no matter which type of user access port system is used, it is necessary to evacuate the glove/arm tube prior to use. Air is conventionally evacuated from the glove/arm tube using a vacuum pump. A pressured inert gas may additionally or alternatively be pumped into the glove/arm tube. Typically, operators are advised to repeat the evacuation process at least twice so as to ensure the air within the glove/arm tube is sufficiently removed.

However, despite the risks associated with spoiling the prescribed atmosphere within a cabinet and the problems associated with restricted movement and touch, it has been found that the evacuation process is sometimes ignored by an operator because it is time consuming and complex.

It has also become apparent that certain operators find the use of the long gloves or arm tubes unnerving and disconcerting because they feel uncontrollably attached to the apparatus. Indeed, the level of agitation may become so significant that an operator may even avoid using a controlled atmosphere apparatus with gloves/arm tubes.

C. SUMMARY OF THE INVENTION

Embodiments of the present invention seek to overcome, mitigate or avoid at least some of the problems discussed above.

A first aspect of the invention relates to a user access port for a controlled atmosphere apparatus comprising:—
a porthole extending through a wall;
a sealing assembly comprising a first sealing means and a second sealing means for maintaining a sealing barrier across the porthole, whereby
the first sealing means comprises a first closure member that is adapted to at least substantially seal the porthole when arranged in a closed position and allow user access to the porthole when arranged in an open position;
the second sealing means is configured so as to extend at least substantially across the porthole and comprises a sealed access member and a second closure member, whereby the sealed access member comprises a user access aperture having a peripheral edge adapted to form a sealing contact with an arm of a user when an operator extends his arm through the user access aperture and whereby the second closure member is adapted to at least substantially seal the user access aperture when arranged in a closed position and at least substantially open the user access aperture when arranged in an open position.

The first sealing means and second sealing means advantageously help to maintain a sealing barrier across the porthole; even if the porthole is accessible to a user, one of the sealing means is open or one of the sealing means has failed.

The second sealing means is advantageously configured to provide sealed user access through the porthole. As a result, the second sealing means at least substantially maintains a seal barrier across the porthole even when a user is extending his hand/arm through the porthole.

In an embodiment, the first closure member may be a movable door adapted to move between a closed position and an open position. Preferably, a lower edge the door is pivotally coupled to the wall so as to rotate between a closed position and an open position.

In an embodiment, the user access port may further comprise locking means to releasably secure the first closure member in a closed position.

In an embodiment, the sealed access member may be a flexible membrane and/or comprises Neoprene.

In an embodiment, the second closure member may be a flexible membrane and/or comprises Neoprene.

In an embodiment, the second closure member may be configured to be biased towards the closed position.

In an embodiment, the second sealing means may comprise locking means adapted to releasably secure the second closure member in a closed position.

In an embodiment, the sealing assembly may comprise a mounting means adapted to mount the second sealing means such that the second sealing means extends at least substantially across the porthole, whereby the mounting means comprises a frame having a centrally located aperture and engaging means to retain the second sealing means such that the second sealing means extends across the centrally located aperture. Preferably the engaging means are releasable engaging means. The mounting means may be arrangeable in a closed position and an open position, whereby the second sealing means extends at least substantially across the porthole when the mounting means is arranged in the closed position and the releasable engaging means are accessible to a user when the mounting means is arranged in the open position. A lower edge of the mounting means may be pivotally coupled to the second surface of the wall so as to rotate between a closed position and an open position. The mounting means may further comprise locking means to releaseably secure the frame in a closed position.

A second aspect of the invention relates to a controlled atmosphere apparatus comprising:— a sealed cabinet having a prescribed atmosphere;

atmosphere controlling means to regulate the prescribed atmosphere in the cabinet; and one or more a user access port according to the first aspect of the invention to provide user access into the cabinet.

A third aspect of the invention relates to a sealing assembly for a user access port having a porthole, the sealing assembly comprising a first sealing means and a second sealing means, whereby the first sealing means comprises a first closure member that is adapted to at least substantially seal a porthole when arranged in a closed position and allow user access to the porthole when arranged in an open position;

the second sealing means is configured so as to extend at least substantially across the porthole and comprises a sealed access member and a second closure member, whereby the sealed access member comprises a user access aperture having a peripheral edge that is adapted to form a sealing contact with an arm of a user when a user extends his arm through the user access aperture and whereby the second closure member is adapted to at least substantially seal the user access aperture when arranged in a closed position and at least substantially open the user access aperture when arranged in an open position.

The sealing assembly may comprise any of the features of the first sealing means and second sealing means according to the first aspect of the invention.

A fourth aspect of the invention relates to a sealing means for sealing a porthole of a user access port, wherein the sealing means is configured to extend at least substantially across the porthole and comprises a sealed access member and a closure member whereby the sealed access member comprises a user access aperture having a peripheral edge that is adapted to form a sealing contact with an arm of a user when a user extends his arm through the user access and whereby the closure member is adapted to at least substantially close the user access aperture when arranged in a closed position and at least substantially open the user access aperture when arranged in an open position.

The sealing means may comprise any of the features of the second sealing means according to the first aspect of the invention.

In an embodiment, the sealing means may be configured to be mounted to extend at least substantially across the porthole using a mounting means.

A fifth aspect of the invention relates to a method of replacing a sealing means of a user access port that is adapted to provide sealed user access into a sealed cabinet of a controlled atmosphere apparatus;

providing a controlled atmosphere apparatus with a first user access port and a second user access port according to the first aspect of the invention;

arranging the first closure member of the first user access port in a closed position so as to at least substantially seal the porthole of the first user access port;

arranging the first closure member of the second user access port in an open position so as to allow access to the user access aperture arranged in the porthole of the second user access port;

extending an arm of a user through the user access aperture of the second user access port into the sealed cabinet and forming a sealing contact with the arm;

arranging the mounting means of the first user access port in an open position so as to provide user access to the releasable engaging means for the sealing means;

removing and replacing the sealing means via the releasable engaging means; and arranging the mounting means of the first user access port in a closed position.

The method may further include the step of retracting the arm of the user from the sealed cabinet via the first user access port.

D. BRIEF DESCRIPTION OF DRAWINGS

For a better understanding of the present invention and to show how it may be carried into effect, reference shall now be made by way of example to the accompanying drawings in which.

E. DETAILED DESCRIPTION OF THE INVENTION

The first aspect of the invention relates to a user access port comprising a porthole and a sealing assembly. The user access port is adapted to provide sealed user access. As a result, a sealing barrier is at least substantially maintained across the porthole so that the flow of fluid through the porthole is at least substantially minimised—even when an operator is extending his hand/arm through the porthole. FIGS. 1-6B depict an embodiment of a user access port (1) comprising a porthole (2) and a sealing assembly (3).

E.1. Porthole

The porthole is essentially an aperture extending through a wall. The aperture extends through the wall from a first surface to an opposing second surface. The aperture is configured to allow an operator's hand and at least a lower portion of the operator's arm to pass at least substantially freely therethrough. The porthole may be a substantially circular, oval or any other suitable shape. The porthole may have a diameter in the range of approximately 12 cm to 20 cm. In the embodiment of the user access port (1) depicted in FIGS. 1-6B, the porthole (2) extends through a wall (4) from an outer surface (41) to an opposing inner surface (42). The porthole (2) is substantially circular in shape and has a diameter of approximately 16 cm.

E.2. Sealing Assembly

The sealing assembly comprises a first sealing means and a second sealing means. Each of the first sealing means and second sealing means is configured to form a sealing barrier across the porthole. The sealing assembly is adapted to at least substantially maintain a sealing barrier across the porthole—even when the porthole is accessible to a user, a user's hand/arm is extending through the porthole, only one of the sealing means is arranged in a closed position or one of the sealing means has failed.

E.2.a First Sealing Means of the Sealing Assembly

The first sealing means is adapted to provide a first sealing barrier across the porthole.

The first sealing means comprises a first closure member that is located adjacent the porthole and may be arranged in a closed position and an open position. The first closure member is configured to form at least a substantially fluid-tight seal across the porthole (a first sealing barrier) when arranged in the closed position. In the open position, the first closure member is configured such that the porthole is at least substantially accessible to allow for user access.

The first closure member may be mounted on the wall or integrally formed with the wall adjacent the porthole.

The first closure member preferably comprises an inner surface and an outer surface. The first closure member is preferably arranged relative to the first surface of the wall, adjacent the porthole.

When arranged in the closed position, the first closure member is configured such that the inner surface of the first closure member extends across the porthole and forms a sealing (mating) contact with the wall. Accordingly, the flow of fluid through the porthole is at least substantially minimised. Preferably, the sealing contact forms a fluid-tight seal that prevents the flow of any fluid through the porthole.

The first closure member is preferably a non-handed or neutral closure member. By providing a non-handed closure member, the closure member may be operated (opened and closed) by either the right hand or the left hand of an operator.

The first closure member may be a door or suitable door-like structure comprising an outer surface and an inner surface. The door is locatable in a closed position to form a first sealing barrier across the porthole and an open position to allow user access to the porthole. The door may be removably mounted and configured to be mountable in a closed position and removable to an open position. The door may be pivotally mounted and configured to be rotatable between a closed position and an open position. The door may be slidably mounted in parallel tracks or guide rails and configured to be slidably movable between a closed position and an open position. The door may alternatively be a foldable door and configured to be foldable between an open position and a closed position. In the embodiment depicted in FIGS. 1-6B, the first closure member is an outer door (5) arranged relative to the outer surface (41) of the wall (4). The outer door (5) comprises a lower edge (51), inner surface (52), outer surface (53) and upper edge (54). The lower edge (51) of the outer door (5) is pivotally coupled to the outer surface (41) of the wall (4) using a hinge such that the outer door is rotatable between a closed position (see FIG. 1) and an open position (see FIG. 2). The outer door is a non-handed door that can be operated by either the right hand or left hand of an operator.

Figure 1:
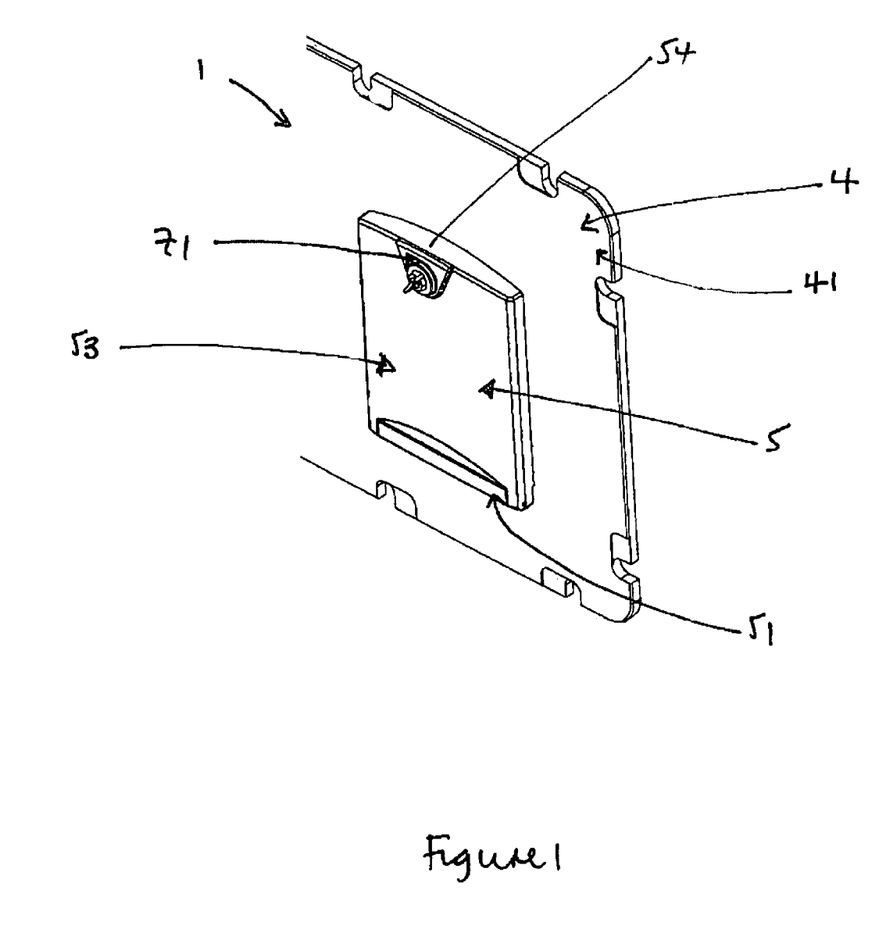
FIG. 1 is a perspective view showing an outer door arranged in a closed position according to an embodiment of a user access port.

FIG. 1 depicts the outer door (5) of the user access port arranged in a closed position so as to form a first sealing barrier across the porthole. It can be seen in FIG. 1 that when the outer door (5) is arranged in a closed position the inner surface (52) of the outer door (5) extends across the porthole (2) and forms a mating (i.e. sealing) contact with the outer surface (41) of the wall, thereby forming a first sealing barrier across the porthole.

Figure 2:
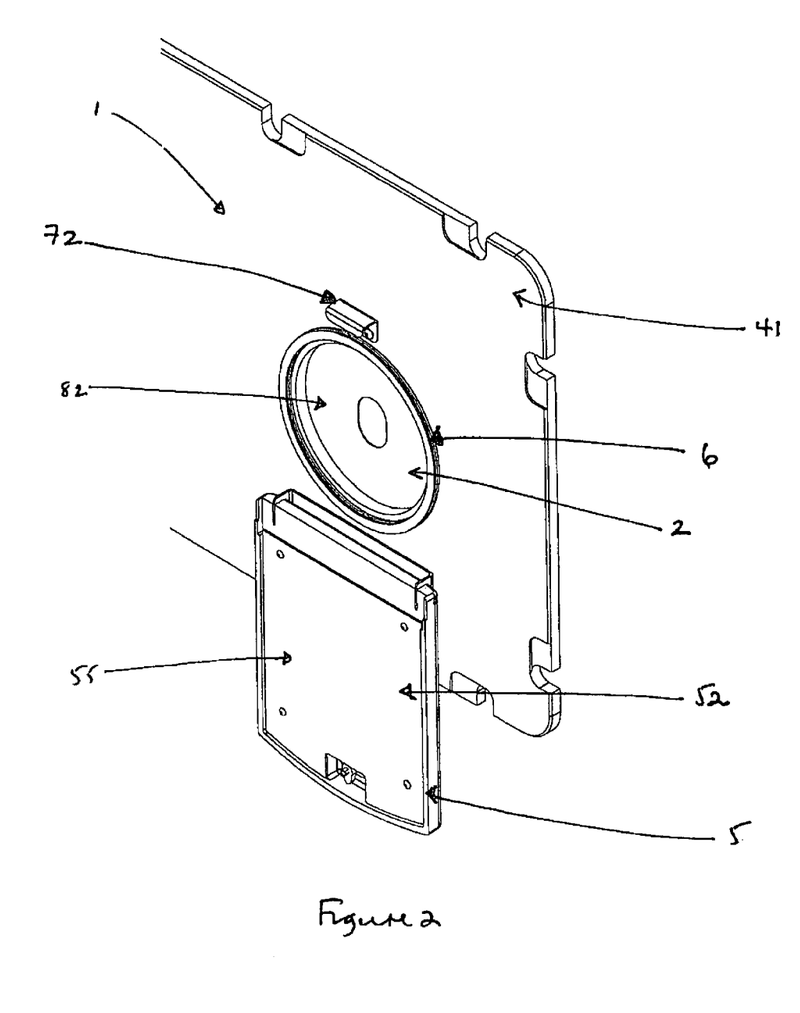
FIG. 2 is a perspective view showing the outer door of the user access port, as depicted in FIG. 1, arranged in an open position.

FIG. 2 depicts the outer door (5) of the user access port arranged in an open position. It can be seen from FIG. 2 that when the outer door is arranged in an open position, the outer door (5) extends in a downwardly direction across the outer surface (41) of the wall and away from the porthole (2) such that the porthole (2) is at least substantially accessible to a user.

The first sealing means may comprise one or more resilient sealing members to help achieve an appropriate sealing contact between the first closure member (e.g. door) and the first surface of the wall. A resilient sealing member may be mounted on the first surface of the wall. Additionally or alternatively, a resilient sealing member may be mounted on an inner surface of the first closure member. The resilient sealing member may be arranged to extend around at least a portion of a peripheral edge of the porthole. The resilient sealing member may be an elastomeric O-ring, lip seal or any other suitable device. In the embodiment depicted in FIG. 2 it can be seen that an elastomeric O-ring (6) is mounted on the outer surface (41) of the wall and arranged circumferentially around a peripheral edge of the porthole (2) so as to help form a fluid-tight seal between an inner surface (52) of the outer door and outer surface (41) of the wall when the outer door (5) is arranged in a closed position.

The first sealing means may comprise locking means to releasably secure the closure member (e.g. outer door) in a closed position and/or open position. The locking means may be adapted so as to help achieve an appropriate sealing contact between the first closure member and the first surface of the wall. The locking means may comprise a rotatable latch member and cooperating retaining member or any suitable locking device. In the embodiment depicted in FIGS. 1-6B, the outer door (5) is releasably securable in a closed position using locking means (7) comprising a rotatable compression latch member (71) and cooperating retaining member (72).

The inner surface of the first closure member is preferably adapted to be suitably rigid and flat so as to help form an appropriate sealing contact with the first surface of the wall. In the embodiment depicted in FIGS. 1-6B, the inner surface (52) of the outer door (5) comprises a substantially smooth and flat metallic plate portion (55) so as to optimise the sealing contact.

The first closure member is preferably configured so as to minimise the disadvantageous effects of creep and thereby help to maintain the sealing contact between the first closure member and wall. For example, in the embodiment depicted in FIGS. 1-6B, the outer surface (51) of the outer door is formed from cast polyurethane with a suitable cross-sectional strength so as to minimise creep.

E.2.b Second Sealing Means of the Sealing Assembly

The second sealing means is adapted to provide a second sealing barrier across the porthole and provide sealed user access through the porthole.

The second sealing means comprises a sealed access member and a second closure member. The second sealing means is arranged so as to extend across the porthole and arranged in a closed position and an open position.

The second sealing means may be a membrane or membrane like structure.

The second sealing means may be mounted relative to the wall so as to extend across the porthole. The second sealing means and first closure member may be mounted on the same side or opposing sides of the wall. If the first closure member is mounted relative to the first surface of the wall, the second sealing means may be mounted relative to the second, opposing surface of the wall.

The second sealing means may be directly mounted on the wall or indirectly mounted with respect to the wall using a mounting means (see below). When mounted relative to the wall, the second sealing means is preferably arranged such that at least a peripheral portion second sealing means (e.g. a peripheral portion of the sealed access member) is arranged in sealing contact with the surface of the wall.

As mentioned above, the second closure member may be arranged in a closed position and an open position. When the second closure member is arranged in the closed position, the second sealing means forms an at least substantially fluid-tight seal (second sealing barrier) across the porthole. When the second closure member is arranged in the open position, the second sealing means allow for sealed user access through the porthole.

E.2.bi. Sealed Access Member of the Second Sealing Means

The sealed access member is configured to provide sealed user access through the porthole when the second closure member is arranged in an open position. More specifically, the sealed access member is configured to maintain a sealing barrier across the porthole when an operator's hand/arm is extending through the porthole.

The sealed access member comprises a first surface, a second opposing surface and a user access aperture extending from the first surface to the second surface.

The user access aperture is configured to allow an operator's hand and at least a lower portion of the operator's arm to pass there through. The user access aperture is preferably centrally located in the porthole.

The sealed access member is adapted such that, when the operator's hand/arm is extended through the user access aperture, a peripheral edge of the user access aperture forms a sealing contact with the skin and/or clothing of the operator. The sealing contact is sufficient to at least restrict or minimise the flow of fluid across the aperture and thereby the porthole. Preferably, the sealing contact is sufficient to form a fluid-tight seal so as to prevent the flow of fluid across the aperture and thereby the porthole. Due to the sealing contact of the sealed access member, a sealing barrier is at least substantially maintained across the porthole when an operator's hand/arm is extended through the user access aperture of the sealed access member.

The sealed access member is preferably adapted to maintain sufficient sealing contact between the peripheral edge of the user access aperture and the skin/clothing of the operator when the operator moves his hand/arm. For example, when the operator is extending or withdrawing his hand/arm through the user access aperture.

The sealed access member is preferably formed from one or more materials that are suitable for forming and maintaining a suitable sealing contact with the skin and/or clothes of operator's wrist/arm. For example, the sealed access member may be formed from a resiliently deformable material. Moreover, the sealed access member is preferably formed from one or more flexible materials so as to allow the operator to move his hand/arm sufficiently freely (without restricted movement) when arranged in sealing contact with the sealed access member.

The sealed access member may comprise one or more layers of material. For example, the sealed access member may comprise a single layered membrane or multiple layered membranes. Whilst a sealed access member having a single layer of material may form a sufficient sealing contact, it has been found that a sealed access member configured to comprise multiple layers of material may provide an improved sealing contact.

The sealed access member may further comprise a resilient sealing means arranged around the peripheral edge of the aperture to enhance the sealing contact with the skin/clothing of the operator. The resilient sealing means may include a sealing lip seal having a 3-D profile. The sealing means may comprise a means having a concertina or bellows-type profile arranged at the peripheral edge region of the user access aperture.

In the embodiment of the user access port depicted in FIGS. 1-6B, the sealed access member (8) is a single layer membrane comprising an inner surface (81), an outer surface (82) and a user access aperture (83). The sealed access member (8) is mounted relative to the inner surface of the wall (42) such that the sealed access member extends across the porthole (2), whereby the inner surface of the sealed access member (81) faces the inner surface of the wall (42) and the outer surface of the sealed access member (82) faces away from the wall (4). The user access aperture (83) of the sealed access member is configured such that the peripheral edge (84) of the aperture forms a sealing contact with the skin/clothing of an operator as he extends his hand/arm through the aperture. In this particular embodiment, the sealed access member (8) is formed from Neoprene so as to form and maintain a suitable sealing contact with the skin/clothing of an operator and so as to be suitably flexible so as to allow the operator to move his hand/arm freely as it extends through the aperture. The sealed access member (8) provides sealed user access via the porthole by forming a sealing contact with the skin/clothing of an operator. Due to the sealing contact, the flow of fluid through the aperture, and thereby through the porthole, is at least minimised.

Since the sealed access member extends across the porthole, the configuration of the sealed access member is dependent on the configuration of the porthole. The sealed access member may have a substantially circular, oval or any suitable shape. The sealing member may have a diameter in the range of approximately 13 cm to 21 cm. In the embodiment depicted in FIGS. 1-6B, the sealed access member (8) has a substantially circular shape with a diameter of approximately 17.5 cm.

The user access aperture of the sealed access member may have a substantially circular, oval or any suitable shape. In the embodiment depicted in FIGS. 1-6B, the aperture (83) of the sealed access member has a substantially oval shape with a maximum diameter of 5.5 cm.

E.2.bii. Second Closure Member of the Second Sealing Means

As mentioned above, the second closure member may be arranged in a closed position and an open position. Preferably, the second closure member is movable between a closed position and an open position.

When arranged in a closed position, the second closure member is configured so as to form an at least a substantially fluid-tight seal across the user access aperture of the sealed access member. Accordingly, the flow of fluid through the user access aperture is at least restricted or minimised when the second closure member is arranged in the closed position. The second sealing means is deemed to form a second sealing barrier across the porthole when the second closure member is arranged in a closed position.

When arranged in an open position, the second closure member is configured so as to open or allow access to the user access aperture, thereby allowing an operator to extend his hand/arm through the user aperture.

The second closure member comprises a first surface and a second surface. The second closure member is arranged with respect to the sealed access member, adjacent the user access aperture. Preferably, the first surface of the second closure member is arranged so as to face the second face of the sealed access member. The second closure member may be mounted in mating contact or integrally formed with the sealing member.

Preferably, the second closure member is configured so that it is biased towards the closed position. Hence, the user access aperture of the sealed access member will remain sealed until the second, closure member is specifically moved to an open position. Moreover, the second closure member will automatically return to the closed position when the actuating force for moving the second closure member is removed. The second closure member may be biased to maintain a sealing contact with the sealed access member by a positive atmospheric pressure differential between either sides of the port wall. The second closure member may be biased to move back to the closed position under the force of gravity.

The second closure member is preferably movable to an open position as an operator pushes his hand/arm against the second closure member so that he can extend his hand/arm through the user access aperture of the sealed access member. If biased towards the closed position, the second closure member will then move back to the closed position as the operator retracts his hand/arm.

The second closure member is preferably formed from one or more materials that are suitable for forming and maintaining a mating (sealing) contact with the sealed access member.

For example, the second closure member may be formed from a resiliently deformable material. Moreover, the second closure member is preferably formed from one or more flexible materials so as to allow an operator to easily move the second closure member. The second closure member may comprise one or more layers of material. For example, the second closure member may comprise a single layered membrane or multiple layered membranes.

The second sealing means may comprise locking means to releasably secure the second closure member in a closed position. Such locking means are preferably adapted to help form the sealing contact between the second closure member and the sealed access member.

The second sealing means may further comprise locking means to releasably secure the second closure member in an open position.

The locking means may comprise one or more magnetic means to maintain the second closure member in a desired position.

Figure 3:
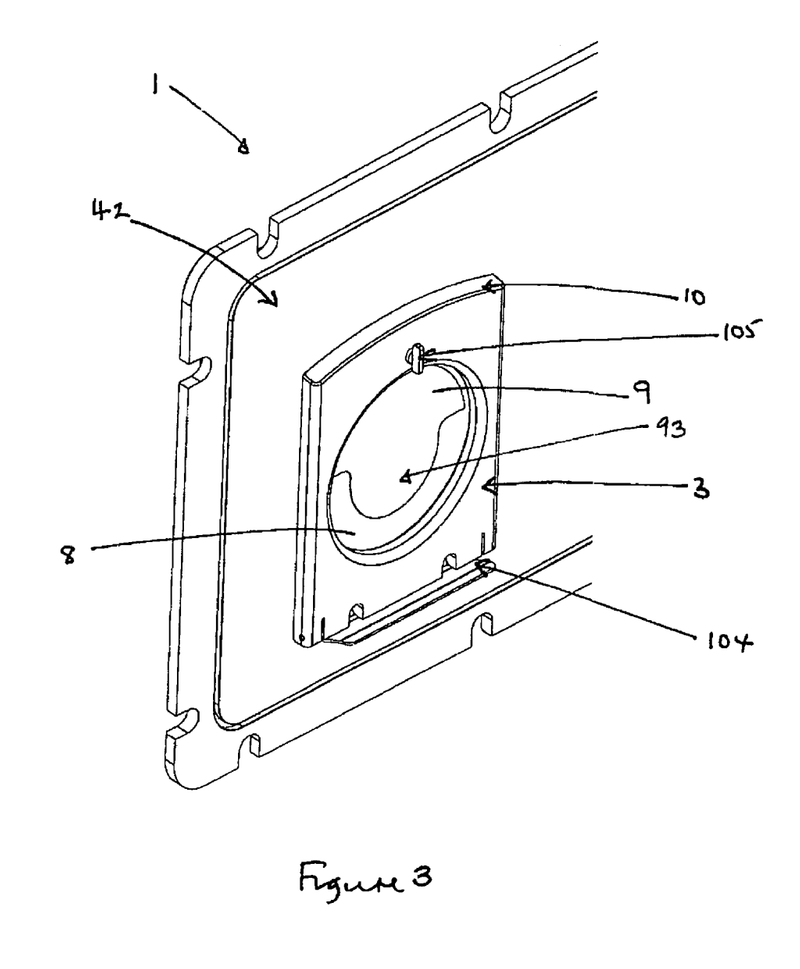
FIG. 3 is a perspective view showing a membrane mounted in a membrane supporting frame, of the user access port as depicted in FIG. 1, when the membrane supporting frame is arranged in a closed position.
Figure 4:
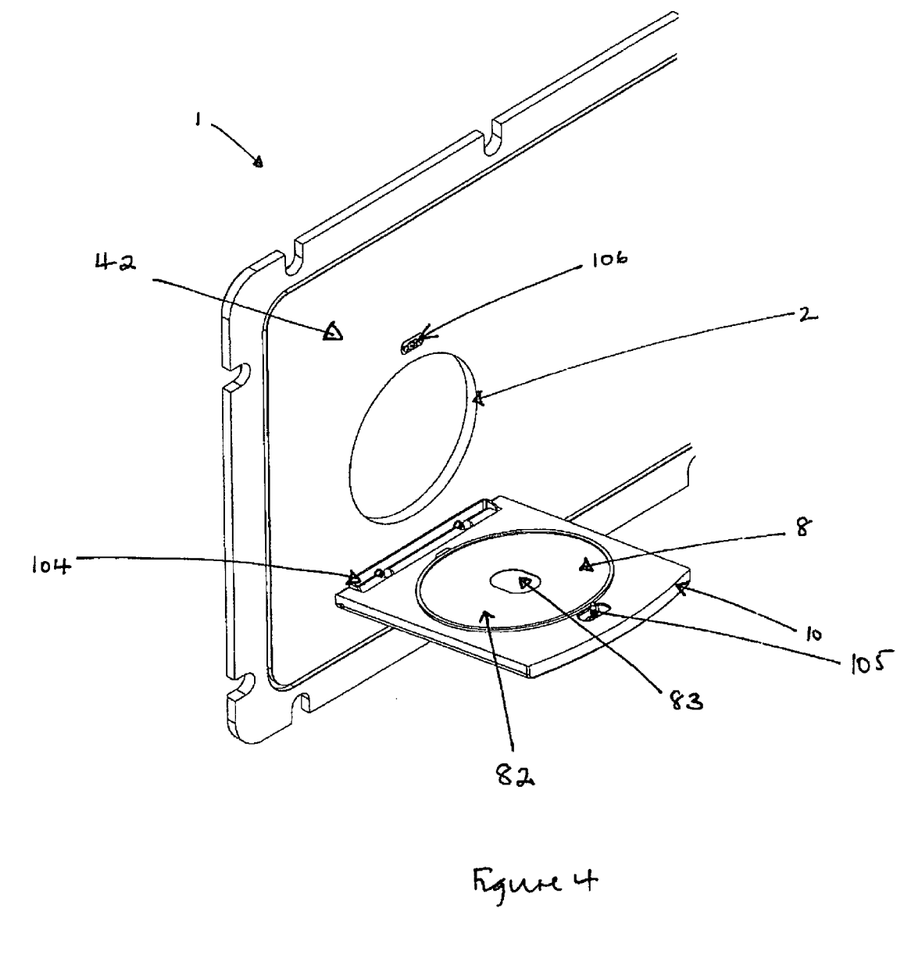
FIG. 4 is a perspective view showing the membrane mounted in the membrane supporting frame, of the user access port as depicted in FIG. 1, when the membrane supporting frame is arranged in an open position.
Figure 5A:
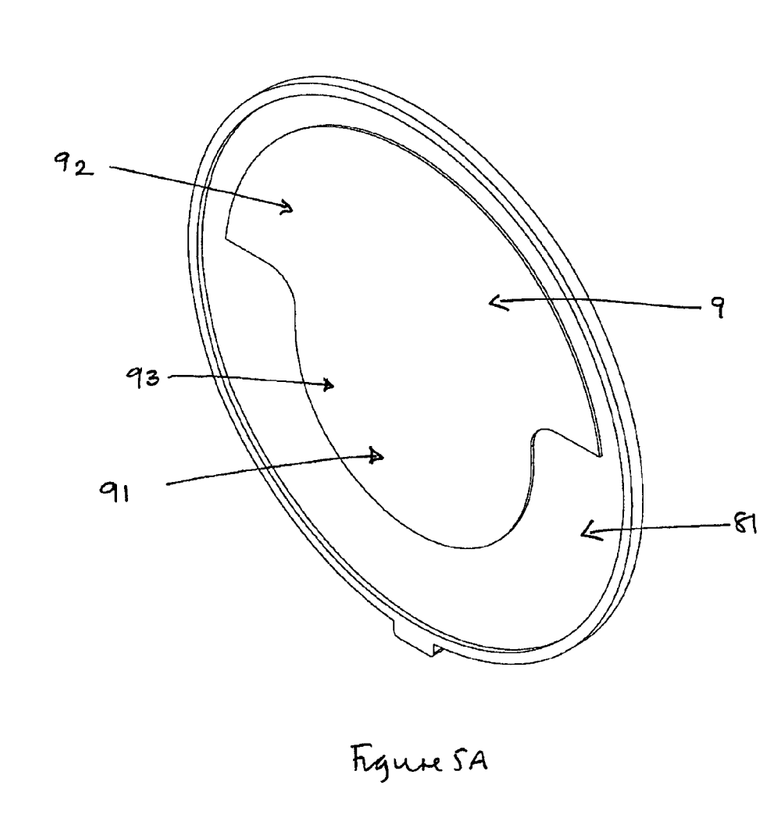
FIG. 5A is a perspective view showing an inner side of the membrane of the user access port as depicted in FIG. 1.
Figure 5B:
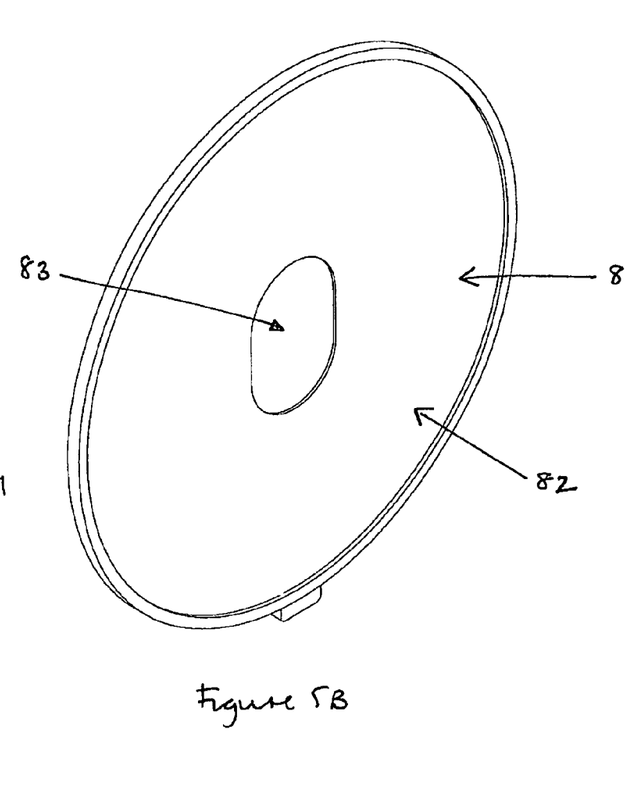
FIG. 5B is a perspective view showing an outer side of the membrane of the user access port as depicted in FIG. 1.
Figure 6A:
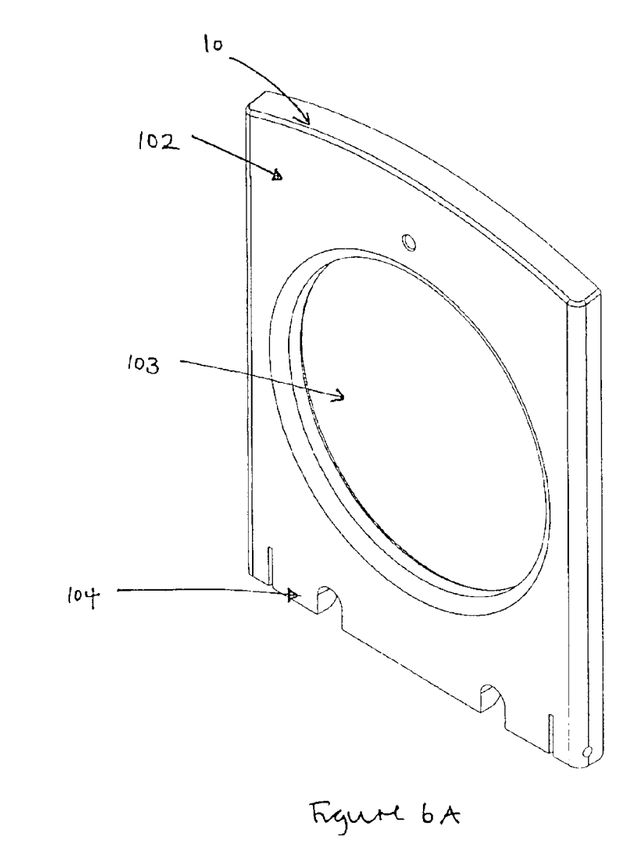
FIG. 6A is a perspective view showing an outer side of the membrane supporting frame of the user access port as depicted in FIG. 1.
Figure 6B:
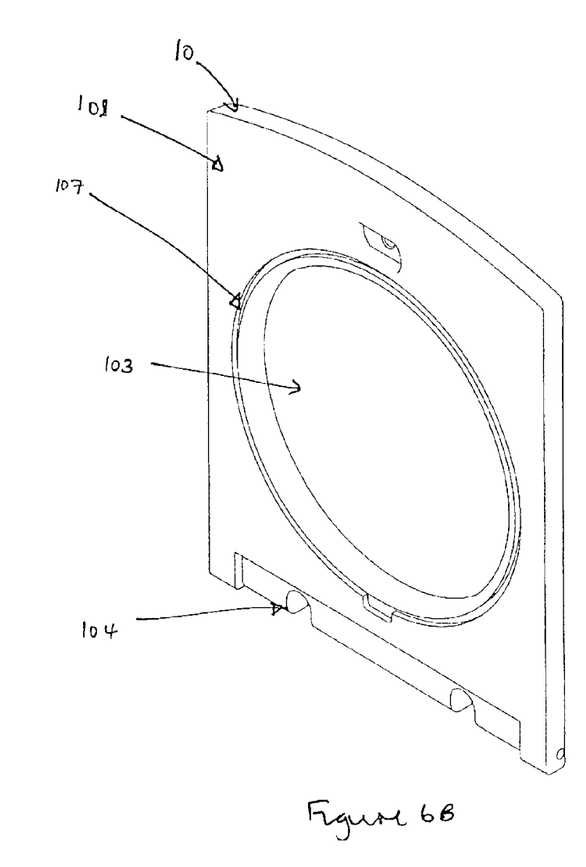
FIG. 6B is a perspective view showing an inner side of the membrane supporting frame of the user access port as depicted in FIG. 1.

In the embodiment depicted in FIGS. 1-6B, the second closure member (9) comprises an outer surface (91) and inner surface (92). FIGS. 3 and 5A depict the second closure member is arranged in a closed position and thereby in sealing contact with the inner surface (81) of the sealed access member. In the closed position, an elongate portion (93) of the second closure member at least substantially extends across and seals the user access aperture (83) of the sealed access member. The second closure member (9) is configured such that it is biased to remain in the closed position until the elongate portion (93) is moved/pushed away from the user access aperture by an operator. The second closure member is moved to an open position as the operator pushes, extends or pulls his hand/arm through the user access aperture (83). In the embodiment depicted, the second closure member (9) is a single layered membrane formed of Neoprene.

E.2.c. Mounting Means of the Sealing Assembly

The sealing assembly may further comprise mounting means adapted so as to mount the second sealing means (sealed access member and second closure member) with respect to the wall such that the second sealing means extends across the porthole.

The mounting means comprises a frame or frame-like structure having a first surface and an opposing second surface. The frame comprises a centrally located aperture extending from the first surface to the second surface. The aperture of the mounting means is configured such that second sealing means at least substantially extends across the aperture when mounted in the mounting means.

The configuration of the aperture is dependent on the configuration of the second sealing means. The aperture may be a substantially circular, oval or other suitable shape. The aperture may have a diameter in the range of approximately 12 cm to 20 cm. The aperture is preferably configured such that when the mounting means is mounted with respect to the wall, the aperture and thereby the second sealing means is juxtaposed with respect to the porthole formed in the wall.

The mounting means further comprises engaging means to retain the second sealing means. The engaging means preferably releasably engage the second sealing means. By releasably engaging the second sealing means, the second sealing means may be replaced or adjusted as and when required. For example, the second sealing means may, be replaced when the peripheral edge of the user access aperture is no longer able to form an appropriate sealing contact with the operator's hand/arm. Preferably, the engaging means is configured so as to releasably engage an outer peripheral edge of the sealed access member. The engaging means may comprise a groove or recess that extends circumferentially around the peripheral edge of the aperture formed in the frame.

The mounting means may be securely mounted with respect to the second surface (inner surface) of the wall. So as to allow for the removal/adjustment/replacement of the second sealing means, the mounting means may be adapted such that it can be arranged in a closed position and an open position.

The mounting means may be adapted to be removably mountable in a closed position and removable to an open position. The mounting means may be removably mounted on the second surface of the wall using any conventional releasable securing/mounting means. When mounted on the wall, the mounting means is arranged such that the second sealing means extends at least substantially across the porthole and the first surface of the mounting means forms a sealing contact with the second surface of the wall. By forming a sealing contact, fluid is at least substantially restricted from flowing between the wall and the mounting means.

Alternatively, the mounting means may be movable between an open position and a closed position so as to allow for the removal/adjustment/replacement of the second sealing means. The mounting means may be pivotally mounted and configured to rotate between an open position and a closed position. The mounting means may be slidably mounted on parallel tracks or guide rails and configured to be slidable between an open position and a closed position. When the mounting means is moved to a closed position, the second sealing means is arranged to extend to across the porthole and the first surface of the mounting means is arranged so as to form a sealing contact with the surface of the wall. The sealing contact is provided so as to at least substantially restrict the flow of fluid between the wall and the mounting means.

When the mounting means is arranged in an open position, the mounting means is arranged to allow for the removal and replacement or adjustment of the second sealing means. Advantageously, the removal and replacement of a second sealing means or adjustment of a second sealing means helps to maintain the sealing barrier across the porthole.

The mounting means may comprise locking means to releasably secure the mounting means in a closed position and/or open position. The locking means may comprise a rotatable latch and cooperating retaining member.

Resilient sealing means may be provided so as to aid the formation of the sealing contact between wall and the mounting means. The resilient sealing means may comprise an elastomeric O-ring, lip seal or any other suitable sealing means. Resilient sealing means may be arranged on the surface of the mounting means and/or the surface of the wall.

The mounting means is preferably a non-handed mounting means that may be operated by either the right hand or left hand of an operator.

The embodiment of the user access port depicted in FIGS. 1-6B comprises a mounting frame member (10) having an outer surface (101), and inner surface (102) and an aperture (103). A bottom edge (104) of the mounting frame Member is pivotally mounted with respect to the inner surface (42) of the wall. As a result, the mounting frame member may be rotated between a closed position and an open position. In the closed position, the mounting frame member is arranged such that the second sealing member at least substantially extends across the porthole (2) and the outer surface (101) of the mounting frame member forms a sealing contact with the inner surface (42) of the wall. In an open position, the mounting frame member is arranged such that it extends away from the inner surface (42) of the wall in a substantially perpendicular direction. In the open position, the outer surface (101) of the mounting frame member is accessible to an operator. By pivotally mounting the mounting frame member along its bottom edge, the mounting frame member is a non-handed mounting frame member because it can be raised into a closed position and lowered into an open position by either the right hand or left hand of the operator. The mounting frame member is releasably securable in the closed position using locking means having a rotatable latch (105) and cooperating retaining means (106). It can be seen in FIGS. 3, 4, 6A and 6B that an outer peripheral edge of the sealed access member (8) of the second sealing member is releasably engaged by a recessed groove (107) formed on an outer surface (101) of the mounting frame member. The second sealing member may be replaced by rotating the mounting frame member to an open position, removing the second sealing means from the mounting frame member, disposing thereof, mounting a further second sealing member on the mounting frame member by pushing the outer peripheral edge of the further second sealing means into the recessed groove and then rotating the mounting frame member into the closed position. Advantageously, a sealing barrier across the user access port will be maintained during the replacement process if the first closure member is arranged in the closed position so as to form a seal across the porthole.

F. Frame

A user access port may further comprise a frame comprising an aperture that defines the user access porthole. The frame and first closure member may be coupled or integrally formed. The frame and the mounting means of the second sealing means may be coupled or integrally formed. The frame may be retrofitted into a wall to define a user access porthole and thereby allow user access from one side of the wall to another.

G. Controlled Atmosphere Apparatus

Figure 7:
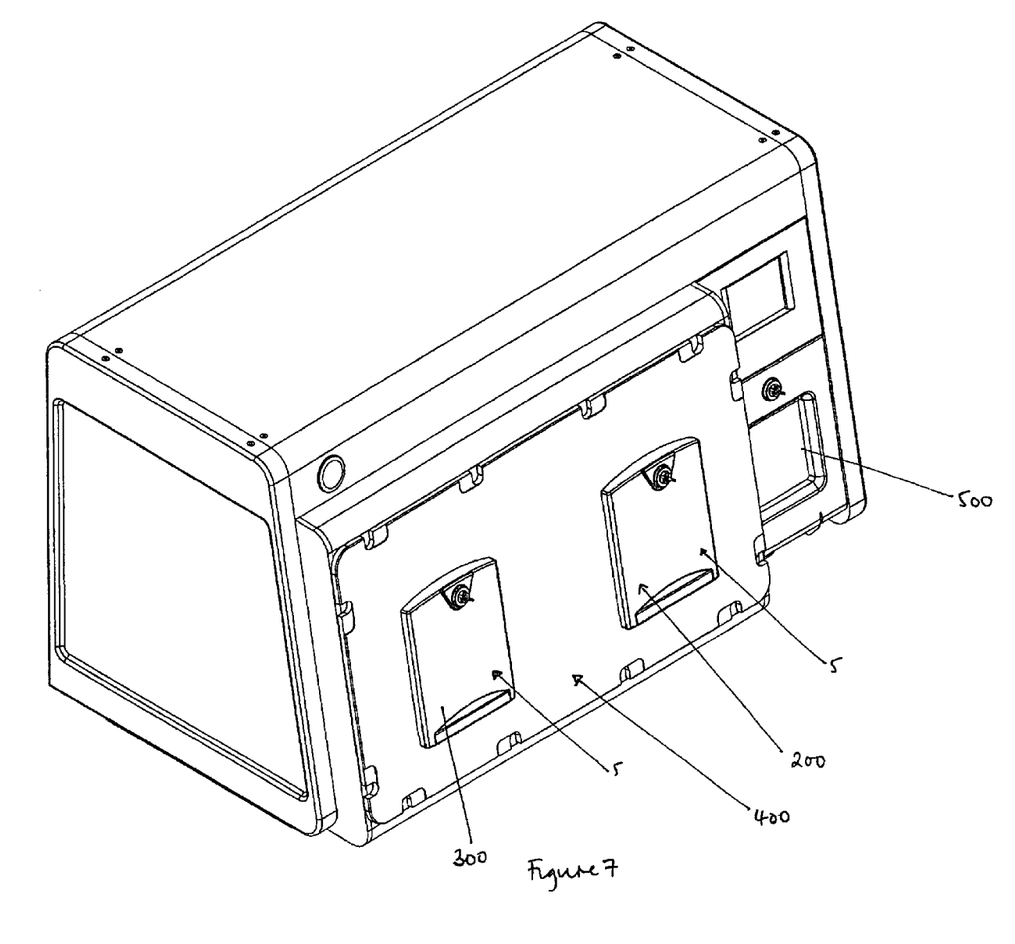
FIG. 7 is a perspective view of a controlled atmosphere apparatus comprising a pair of user access ports according to an embodiment of a second aspect of the invention.
Figure 8:
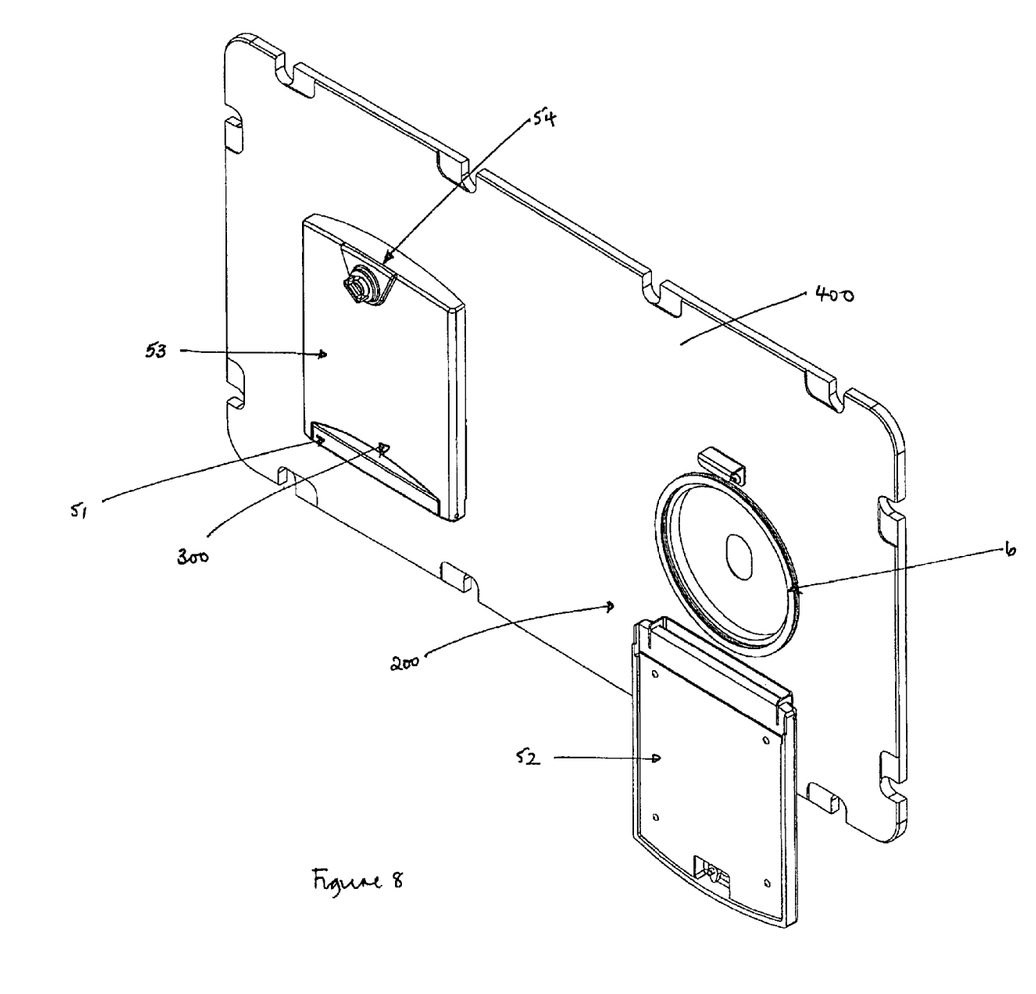
FIG. 8 is a perspective view showing an outer side of a removable wall portion of the controlled atmosphere apparatus as depicted in FIG. 7.
Figure 9:
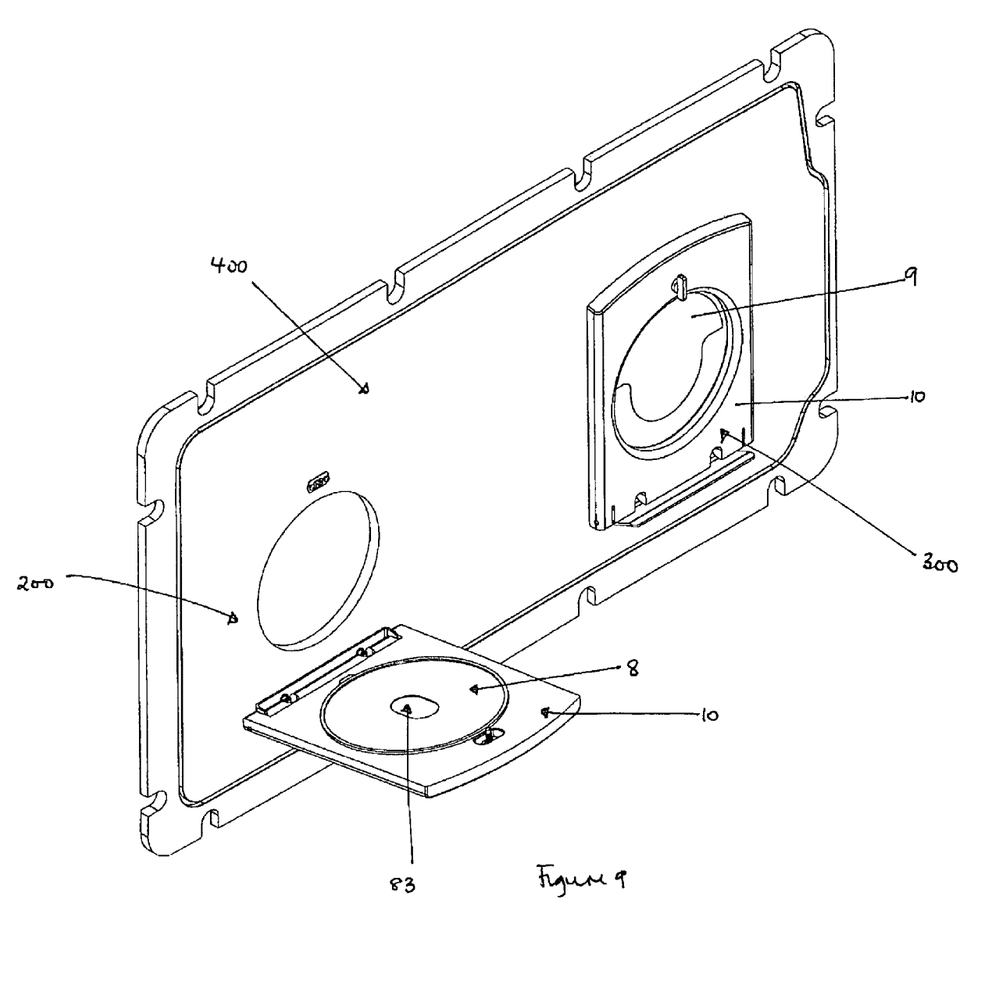
FIG. 9 is a perspective view showing an inner side of the removable wall portion of the controlled atmosphere apparatus as depicted in FIG. 7.

The second aspect of the invention relates to controlled atmosphere apparatus comprising at least one user access port. As explained above, the user access port is adapted to at least substantially maintain a sealing barrier across the porthole. As a result, the user access port is able to provide sealed user access into the controlled atmosphere apparatus such that an operator can manipulate samples inside the controlled atmosphere apparatus without at least substantially altering a prescribed atmosphere within the controlled atmosphere apparatus. FIGS. 7-9 depict an embodiment of a controlled atmosphere apparatus comprising two user access ports.

The controlled atmosphere apparatus comprises at least one sealed cabinet or chamber adapted to have a prescribed atmosphere. The prescribed atmosphere within the cabinet is dependent on the use of the controlled atmosphere apparatus. For example, the controlled atmosphere apparatus may be required to provide normoxic, hypoxic, anoxic or anaerobic environmental conditions.

The prescribed atmosphere is created and maintained within the cabinet by atmosphere controlling means. The atmosphere controlling means preferably provides and controls the prescribed atmosphere within the cabinet by controlling the gas concentrations, temperature and/or humidity within the cabinet.

The atmosphere controlling means typically provide a prescribed atmosphere within the cabinet having a higher pressure than the ambient room pressure. This is provided to help minimise or prevent the ingress of the external atmosphere into the sealed cabinet. Moreover, the positive pressure differential between the sealed cabinet and the external room/laboratory helps to form a sealing contact between the second closure member and the sealed access member when the second closure member is arranged in a closed position.

The atmosphere controlling means may comprise gas control means to regulate the gas concentration(s) within the cabinet. The gas control means may comprise one or more gas sources, gas sensors to detect the gas/gas mixture within the cabinet and gas regulating (e.g. valves) to regulate the flow of gas into and out of the cabinet as required. The atmosphere controlling means may comprise temperature control means to regulate the temperature within the cabinet. The temperature control means may comprise temperature sensing means to detect the temperature within the cabinet and heating/cooling means to increase or decrease the temperature within the cabinet as required. The atmosphere controlling means may comprise humidity control means to regulate the humidity within the cabinet. The humidity control means may comprise a dehumidification system to sense the humidity level within the cabinet and having moisture regulating means to increase or decrease the humidity within the cabinet as required.

The atmosphere controlling means may comprise a microprocessor-based operating system to control the gas control means, temperature control means and/or humidity control means. The required gas concentrations, temperature and/or humidity may be factory set and non-adjustable. However, the atmosphere controlling means may further include user selectable features to allow an operator to select or adjust the prescribed atmosphere with the cabinet. For example, the atmosphere controlling means may allow a user to set, maintain and control the gas concentrations, temperature and/or humidity within the chamber. The atmosphere controlling means preferably comprise manually operable means to set, maintain and control the prescribed atmosphere. For example, the microprocessor-based operating system may comprise a touch screen display system to allow a user to select, adjust and monitor the gas concentration, temperature and/or humidity within the cabinet.

The controlled atmosphere apparatus may further comprise an airlock to allow for the introduction and/or removal of items, samples vessels (e.g. Petri dishes), equipment and/or instrumentation to and from the sealed chamber. The airlock is adapted to permit the rapid transfer of samples and other items to and from the cabinet without compromising the prescribed atmospheric conditions within the cabinet.

The airlock preferably comprises a small chamber fitted with an outer door (preferably a hinged outer door) and an inner door (preferably a sliding inner door). The inner door is positioned between the airlock and the sealed cabinet. The inner door is designed to provide a primary barrier between the cabinet and laboratory/room conditions and should always be closed and sealed except when items are being introduced or removed. The airlock is typically equipped with a number of safety interlocks to prevent the inadvertent loss of chamber conditions.

An airlock cycle can be started by either touching the chamber/airlock symbol on the touch screen display or by pressing a button located inside the cabinet. The outer door may be manually opened and closed. The latch is preferably manually rotated clockwise to seal the door and counter-clockwise to open the door. Pressing the button located inside the cabinet releases the inner door. This action deflates the door seal and allows the door to glide slowly under the effects of gravity towards the back of the cabinet. The inner door may be closed manually by pulling it gently into the closed position and briefly holding the door until a sensor registers that the door is in the correct position. The door seal then inflates automatically.

The airlock cycle preferably takes approximately 60 seconds. During the airlock cycle, the airlock is flushed with an appropriate gas depending on the prescribed atmospheric mode of the cabinet.

The method, means and apparatus required to provide a prescribed atmosphere within a cabinet are well known to the person skilled in the art and will not be discussed in detailed.

The controlled atmosphere apparatus may comprise one or more user access ports according to the first aspect of the invention to provide user access into the controlled atmosphere apparatus. The one or more user access ports may be configured to allow for sealed user access into the sealed cabinet. A user access port may be configured to allow for sealed user access into the cabinet such that an operator can manually operate the internal push button and/or the inner door of the airlock.

As explained above, the use of two sealing means optimises the sealing of the user access port because a sealing barrier will be at least substantially maintained across the porthole even when one sealing means is arranged in an open position or has failed. The second sealing means is advantageously configured to provide sealed user access via the porthole. The sealed user access is sufficient to at least minimise the ingress of the external atmosphere into the cabinet and also at least minimise the escape of the internal atmosphere from the cabinet when an operator extends his hand/arm into the cabinet via the port. As a result, the cabinet remains at least substantially sealed and the prescribed atmosphere within the cabinet is at least substantially maintained when accessed by an operator.

The controlled atmosphere apparatus may comprise one or more user access port. For example, the controlled atmosphere apparatus may comprise a pair of user access ports configured to simultaneously allow an operator to have both right-handed and left-handed access into controlled atmosphere apparatus. The controlled atmosphere apparatus may comprise an even number of user access ports, preferably arranged in pairs. If the controlled atmosphere apparatus comprises an odd number of user access ports preferably at least one of the user access ports is a non-handed access port. For example, the controlled atmosphere apparatus may comprise a pair of user access ports arranged in a first wall and a third non-handed user access port in a second wall.

The controlled atmosphere apparatus may comprise at least one removably mounted wall portion so as to, provide an aperture in the wall of the controlled atmosphere apparatus. The removably mounted wall portion may be arranged so as allow ease of access into the sealed cabinet when the controlled atmosphere apparatus is not in use. For example, a removably mounted wall portion may be provided to allow for the transfer of items, sample vessels, equipment and/or instrumentation to and from the sealed cabinet. In this case, the removably mounted wall portion and aperture in the wall are preferably configured to allow for the transfer of items that are too large or bulky to be transferred via the airlock. The removably mounted wall portion may be alternatively or additionally provided to allow for the cleaning of the sealed cabinet.

The removably mounted wall portion is removably mounted using any suitable releasable securing/mounting means. For example, the releasable mounting means may comprise a rotatable latch and cooperating retaining member or recess. One or more releasable mounting means preferably arranged around the peripheral edge region of the removable wall portion and/or the peripheral edge region of the aperture.

When mounted in the wall of the controlled atmosphere apparatus, the removably mounted wall portion is adapted such that a portion of an inner surface of the wall portion forms a sealing contact with the peripheral edge region of the aperture.

Resilient sealing means may be provided so as to aid the formation of the sealing contact between the inner surface of the wall portion and the peripheral edge region. The resilient sealing means may comprise an elastomeric O-ring, lip seal or any other suitable sealing means. Resilient sealing means may be arranged on the inner surface of the wall portion and/or the peripheral edge region of the aperture in the wall.

The removably mounted wall portion may comprise one or more user access ports according to the first aspect of the invention.

FIGS. 7 to 9 depict a controlled atmosphere apparatus (A) comprising a pair of user access ports, first user access port (200) and second user access port (300). The user access ports (200, 300) comprise the same features as the embodiment depicted in FIGS. 1-6B. The user access ports (200, 300) are formed in a removably mounted wall portion (400) arranged in a front wall of the controlled atmosphere apparatus so as to provide access into the sealed cabinet. The user access ports are configured such that an operator may simultaneously access the cabinet using both his right hand/arm and left hand/arm. However, the user access ports are non-handed user access ports such that an operator may use his right hand or left hand to operate either user access ports. The first user access port (200) is located close to an airlock (500) such that an operator may access the push button to release the inner door of the airlock and optionally manually open/close the inner door.

The user access ports (200, 300) are also configured such the an operator may gain access through one particular user access port so as to remove, adjust and replace the second sealing means of the other user access port. Due to the sealing access features of the user access ports, the second sealing member of a user access port may be removed, adjusted or replaced without at least substantially compromising the prescribed atmosphere in the cabinet. For example, when the first closure member of the second user access lock (300) is arranged in the closed position, an operator may extend his arm through the first user access port (200) to open the mounting frame member of the second user access port (300), remove and replace the second sealing means of the second user access port (300) and finally close the mounting frame member of the second user access port without there being any substantial alteration in the prescribed atmosphere in the cabinet. The operator may remove the old second sealing means by carrying it through the first user access port as he, retracts his arm/hand. Likewise, the operator may introduce the new second sealing means into the cabinet by carrying it through the first user access port as he inserts his hand/arm. Alternatively, the operator may remove the old second sealing means and/or introduce the new second sealing means via the airlock.

It will be apparent to a skilled person that the invention relates to improved user access via a user access port. The user access port does not require evacuation prior to use. The user access port provides "bare hand" access and so the movement of the user is not restricted, the user's sensitivity of touch is not limited and the user's hands do not become clammy. Moreover, the disconcerting feelings due to wearing gloves/arm tubes are avoided.

The user access port is able to at least substantially maintain a seal barrier across the porthole so as to at least minimise the flow of fluid through the porthole. For example, the user access port is able to at least substantially maintain a seal barrier when the porthole is not in use. Moreover, the user access port is able to at least substantially maintain a seal barrier when an operator has extended his hand/arm through the porthole.

Advantageously, the user access port is configured to allow for the removal, adjustment and replacement of a sealing means.

Throughout the description and claims of this specification, the words "comprise" and "contain" are variations of the words, for example "comprising" and "containing", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The structural arrangement and use of subsection headings within the description is not intended to limit the scope of the invention or exclude any combination of features unless the context requires.

The invention claimed is:

1. A user access system for a controlled atmosphere apparatus comprising:
   a wall having a porthole extending through the wall;
   a first sealing assembly comprising a first closure member that is adapted to at least substantially seal the porthole when arranged in a closed position and allow user access to the porthole when arranged in an open position; and
   a second sealing assembly mounted so as to extend at least substantially across the porthole and comprising a sealed access member having a peripheral edge that defines a user access aperture having a smaller diameter than the porthole and forms a sealing contact with an arm of an operator when the operator extends the arm through the user access aperture, and a second closure member that substantially extends across the diameter of the user access aperture when arranged in a closed position thereby substantially sealing the user access aperture, wherein the second closure member moves, in response to the operator extending the arm through the porthole, to an open position in which the second closure member does not substantially extend across the diameter of the user access aperture.

2. The user access system according to claim 1 further comprising a fastener configured to releasably secure the first closure member in the closed position.

3. The user access system according to claim 1, wherein the sealed access member is a flexible membrane and comprises Neoprene.

4. The user access system according to claim 1, wherein the second closure member is a flexible membrane and comprises Neoprene.

5. The user access system according to claim 1, wherein the second closure member is configured to be biased towards the closed position.

6. The user access system of claim 1, wherein the second sealing assembly further comprises a fastener adapted to releasably secure the second closure member in a closed position.

7. The user access system of claim 1, wherein the second closure member comprises an elongated portion configured to at least substantially extend across and seal the user access aperture and further configured to be moved away from the user access aperture when the operator extends the arm through the user access aperture.

8. The user access system according to claim 1 wherein the first closure member is a movable door adapted to move between a closed position and an open position.

9. The user access system according to claim 8 wherein a lower edge the door is pivotally coupled to the wall so as to rotate between a closed position and an open position.

10. The user access system of claim 1, further comprising a mount adapted to mount the second sealing assembly with respect to the wall such that the second sealing assembly extends at least substantially across the porthole, whereby the mount comprises a frame having a centrally located aperture and a retainer configured to retain the second sealing assembly such that the second sealing assembly extends across the centrally located aperture.

11. The user access system of claim 10, wherein the retainer is configured to releasably retain the sealed access member.

12. The user access system of claim 11, wherein the retainer is a groove extending circumferentially around an edge of the centrally located aperture of the frame.

13. The user access system of claim 12, wherein a lower edge of the mount is pivotally coupled to the wall so as to rotate between a closed position and an open position.

14. The user access system of claim 12, wherein the mount comprises a fastener configured to releaseably secure the frame in a closed position.

15. A sealing assembly comprising a first sealing means and a second sealing means, whereby the first sealing means comprises a first closure member that at least substantially seals a porthole when arranged in a closed position and allow user access to the porthole when arranged in an open position; the second sealing means comprises a sealed access member and a second closure member, whereby the sealed access member defines a user access aperture having a smaller diameter than the porthole and having a peripheral edge that forms a sealing contact with an arm of a user when the user extends the arm through the user access aperture and whereby the second closure member is adapted to at least substantially seal the user access aperture when arranged in a closed position and at least substantially open the user access aperture when arranged in an open position, wherein the second closure member moves, in response to the user extending the arm through the user access aperture, to an open position in which the second closure member does not substantially extend across the diameter of the user access aperture.

16. A controlled atmosphere apparatus comprising:
a wall having a porthole extending through the wall from a first surface to a second surface;
a sealed access membrane mounted so as to extend at least substantially across the porthole, the sealed access membrane defining a user access aperture having a smaller diameter than the porthole and having a peripheral edge configured to form a sealing contact with an arm of a user when the arm is extended through the user access aperture; and
a closure membrane mounted so as to extend at least substantially across the user access aperture when in a closed position thereby sealing the user access aperture and moves away from the user access aperture to an open position when the arm of the user is extended through the user access aperture in which the closure membrane does not substantially extend across the diameter of the user access aperture when in the open position.

17. The apparatus of claim 16, further comprising an outer door mounted to the first surface of the wall, wherein the outer door is configured to move between a closed position and an open position, wherein the outer door extends across the porthole and is in sealing contact with the first surface of the wall when in its closed position, and wherein the outer door allows access to the user access aperture when in its open position.

18. The apparatus of claim 16, wherein the closure membrane is configured to be biased towards its closed position.

19. The apparatus of claim 18, further comprising an inner door mounted to the second surface of the wall and configured to mount the sealed access membrane and the closure membrane, wherein the inner door is further configured to move between a closed position and an open position, the sealed access membrane and closure membrane extending substantially across the porthole when the inner door is in the closed position.

20. The apparatus of claim 19, wherein the closure membrane is configured to be removable from the inner door when the inner door is in its open position.

* * * * *